US006333162B1

(12) United States Patent
Kondo et al.

(10) Patent No.: US 6,333,162 B1
(45) Date of Patent: *Dec. 25, 2001

(54) METHOD FOR MEASURING CHOLINESTERASE AND METHOD FOR DISTINGUISHING BETWEEN LIVER CIRRHOSIS AND HEPATITIS

(75) Inventors: Masahide Kondo, Zama; Kiyoshi Yasukawa, Sagamihara; Toshikazu Hada, Ikoma, all of (JP)

(73) Assignee: Tosoh Corporation, Yamaguchi-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/632,326

(22) Filed: Apr. 17, 1996

(30) Foreign Application Priority Data

Apr. 18, 1995 (JP) ...................................... 7-092401

(51) Int. Cl.[7] .............. C12Q 1/00; G01N 33/48
(52) U.S. Cl. .............. 435/7.1; 435/4; 435/7.92; 435/7.4
(58) Field of Search .................. 435/7.92, 7.4, 435/7.1, 4

(56) References Cited

U.S. PATENT DOCUMENTS

| | | | |
|---|---|---|---|
| 3,654,090 | * | 4/1972 | Wilhelmns et al. |
| 4,281,061 | * | 7/1981 | Zuk et al. ................. 435/7 |
| 4,289,747 | * | 9/1981 | Chu ......................... 424/1 |
| 4,474,878 | * | 10/1984 | Halbert et al. ........... 435/7 |
| 4,931,385 | * | 6/1990 | Block et al. ............. 435/7 |

FOREIGN PATENT DOCUMENTS

| | | |
|---|---|---|
| A0387861 | 9/1990 | (EP) . |
| A0441470 | 8/1991 | (EP) . |
| A 30620 | 9/1991 | (JP) . |

OTHER PUBLICATIONS

Itou et al, Clinica Chimica Acta, vol. 207, (1992), pp. 11–18.*
Ohkura et al, Cancer Res., 54:55–61 (1994).
Nature, vol. 256, (1975), pp. 495–497, "Continuous cultures of fused cells secreting antibody of predefined specificity", G. Kohler et al.
J. Clin. Chem. Clin. Biochem., vol. 28, (1990), pp. 221–224, "Enzyme Immunoassay of Human Cholinesterase (EC 3.1.1.8) Comparison . . . Samples from Healthy Individuals", A. Brook et al.
Hum Hered, vol. 40, (1990), pp. 153–158, "Heterogeneity of the Silent Gene for Plasma Cholinesterase", M. Whittaker et al.
Cancer Research, vol. 54, (1994), pp. 55–61, "Increase of Fucosylated Serum Cholinesterase in Relation to High Risk Groups for Hepatocellular Carcinomas", T. Ohkura et al.
Molecular Pharmacology, vol. 24, (1983), pp. 513–520, "Production and Characterization of Separate Monoclonol Antibodies to . . . Butyrylcholinesterase", S. Brimijoin et al.
Scand J Clin Lab Invest, vol. 51, (1991), pp. 349–358, "Quantification and phenotyping of serum cholinesterase by enzyme antigen immunoassay: . . . applicability", J. Hangaard et al.
Progress in Clinical Biochemistry, (1992), pp. 381–383, "Enzyme immunoassay for serum cholinesterase", T. Hada et al.
Analytical Biochemistry, vol. 165, (1987), pp. 320–326, "Lectin–Enzyme Immunoassay of Transferrin Sialovariants Using Immobilized . . . Ricinus communis", J.M. Pekelharing et al.
Clinica Chimica Acta, vol. 179, (1989), pp. 143–152, "α–Fetoprotein antibody–lectin enzyme immunoassay to characterize . . . liver diseases", N. Kinoshita et al.
Cancer Research, vol. 51, (1991), pp. 5888–5892, "Glycosylation at the Fab Portion of Myeloma Immunoglobulin G and . . . Lens culinaris Agglutinin", N. Kinoshita et al.
Clinica Chimica Acta, vol. 243, No. 1, (1995), pp. 1–9, "Enzyme–linked immunosorbent assay (ELISA) for Aleuria aurantia lectin–reactive serum cholinesterase to . . . chronic hepatitis", M. Kondo et al.
Chemical Abstracts, vol. 118, No. 11, (1993), pp. 342, No. 96 918j, "The peptidase activity of human serum butyrylcholinesterase; . . . the peptidase", Columbus, Ohio, USA R.V. RAO et al.
Patent Abstracts of Japan, C section, vol. 16, No. 93, (1992), p. 140 C917, unexamined applications.
Patent Abstracts of Japan, C section, vol. 14, No. 566, (1990), p. 55 C789, unexamined applications.
Patent Abstracts of Japan, C section, vol. 14, No. 188, (1990), p. 9 C 710, unexamined applications.

* cited by examiner

Primary Examiner—Bennett Celsa
(74) Attorney, Agent, or Firm—Sughrue Mion, PLLC

(57) ABSTRACT

The object of the present invention is to provide method for discriminating between liver cirrhosis and chronic hepatitis by serodiagnosis using a simple enzyme immunoassay method without performing histopathological examinations by biopsy and so forth.

The present invention discloses an enzyme immunoassay method for cholinesterase using monoclonal antibody, a method for detecting *Aleuria aurantia* lectin-reactive cholinesterase using monoclonal antibody and *Aleuria aurantia* lectin, and a method for discriminating between liver cirrhosis and chronic hepatitis on the basis of those results.

5 Claims, 2 Drawing Sheets

METHOD FOR MEASURING CHOLINESTERASE AND METHOD FOR DISTINGUISHING BETWEEN LIVER CIRRHOSIS AND HEPATITIS

BACKGROUND OF THE INVENTION

1. Field of the Invention

The present invention relates to a method for measuring total cholinesterase in, for example, serum; a method for measuring *Aleuria aurantia* lectin-reactive cholinesterase in, for example, serum; and an in vitro diagnostic method for distinguishing liver cirrhosis, liver carcinoma and hepatitis using those methods.

2. Related Art

Two types of cholinesterase exist in the body that differ in terms of enzymological properties, physiological function and distribution in the body. Namely, the first is acetylcholinesterase (E.C.3.1.1.7), which specifically breaks down acetylcholine, exists in a large amount in erythrocytes, neural tissue, muscle and so forth, and is distributed in relation to these physiological functions. The other is cholinesterase (also referred to as pseudocholinesterase or butylcholinesterase) (E.C.3.1.1.8), which acts on cholines, such as benzoylcholine and butylcholine, exists in a large amount in the serum and liver, is produced in the liver, and the physiological action of which is considered to most likely be involved with the neuromuscular system.

At present, the cholinesterase that is frequently measured in clinical laboratory examinations is cholinesterase in serum (pseudocholinesterase or butylcholinesterase). This enzyme is a glycoprotein having a molecular weight of approximately 340,000 and is composed of four identical subunits. Each subunit is composed of 574 amino acids and has nine asparagine-coupled carbohydrate chains. Clinically, a decrease in its activity, as determined by measuring this enzyme, has significance in terms of determining the degree of functional impairment the liver parenchyma in liver disease, and particularly chronic liver parenchymal disorders such as liver cirrhosis and chronic hepatitis. Since serum cholinesterase is produced in liver parenchymal cells, its decrease indicates a chronic functional decrease of liver cells. In addition, acute decreases in cholinesterase activity are observed in cases of poisoning by organic phosphorous-based agricultural chemicals, measurement of the activity of this enzyme is indispensable in these cases. In addition, increases in the activity of this enzyme are observed prominently in nephrotic syndromes.

In the past, measurement of cholinesterase was performed by various methods including a thiocholine method, wherein thiocholine released by cholinesterase is measured by coloring it with an SH group assay reagent using the synthetic substrates of acetylthiocholine, propionylthiocholine and butylthiocholine; a UV method wherein a direct decrease in substrate is measured in the form of the reduction in absorbance of the ultraviolet using benzylcholine as the substrate; a pH colorimetric method wherein an organic acid produced by cholinesterase is measured using a pH indicator; and an enzyme method (cholinoxidase method) wherein the hydrogen peroxide produced during specific decomposition of choline by cholinesterase is measured with a coloration system using benzoylcholine as the substrate and cholinoxidase and peroxidase as cooperative enzymes.

In addition, ever since the development of technology for producing monoclonal antibodies by G. Kohler and C. Milstein in 1975 (Nature, Vol. 256, p. 495, 1975), numerous monoclonal antibodies have been prepared for various antigens. The use of monoclonal antibodies has proceeded in the fields of in vitro diagnostic drugs, in vivo diagnostic drugs, therapeutic drugs and affinity purification reagents. Some of these have already reached the level of practical application, while research and development are being actively conducted, on others, to reach practical application.

Monoclonal antibodies to cholinesterase have also been produced. Examples of methods that have already been reported include a method wherein cholinesterase is measured by an enzyme immunoassay method using immobilized polyclonal antibody to cholinesterase and monoclonal antibody to cholinesterase (A. Broch, et al., J. Clin. Chem. Clin. Biochem., Vol. 28, p. 222, 1990), and a method wherein cholinesterase is measured by an enzyme immunoassay method using immobilized monoclonal antibody to cholinesterase and polyclonal antibody to cholinesterase (M. Whittaker, et al., Hum. Hered, Vol. 40, p. 153, 1990).

*Aleuria aurantia* lectin is a protein that is free of carbohydrate chains prepared from *Aleuria aurantia*. It contains large amounts of serine and glycine, has a molecular weight of 72,000 and has subunits having a molecular weight of 31,000. It has one carbohydrate binding site per subunit. It has affinity for L-fucose as a -monosaccharide. The lectin binds with $\alpha 1 \rightarrow 2$ L-fucose and $\alpha 1 \rightarrow 3$ L-fucose residues, and binds strongly with a carbohydrate chain having an $\alpha 1 \rightarrow 6$ L-fucose residue.

Recently, a serum was treated by chromatography using an affinity column on which *Aleuria aurantia* was immobilized (T. Ohkura and T. Hada et al.) When this column was used to measure the enzyme activity of *Aleuria aurantia* lectin-reactive cholinesterase retained on the column and to determine the ratio of that cholinesterase to the total enzyme activity of cholinesterase originally present in the serum, that ratio was indicated as being significantly higher in patients with hepatocellular carcinoma and liver cirrhosis than in patients with chronic hepatitis and normal controls (Cancer Research, Vol. 54, p. 55, 1994). In addition, there is no other method at present for diagnosing liver cirrhosis and chronic hepatitis than by performing histological examinations of liver tissue specimens obtained by biopsy or operation, thus causing a considerable burden on patients.

SUMMARY OF THE INVENTION

Methods for measuring cholinesterase of the prior art, including the thiocholine method, UV method, pH colorimetric method and enzyme method (cholinoxidase method), all measure the enzyme-activity of cholinesterase, and do not measure the amount of cholinesterase as protein.

In addition, in the case of methods that measure enzyme activity, depending on the selection of the substrate, there is the possibility of also measuring the activity of substances (enzymes) other than cholinesterase that have esterase activity. Since that which appears as a result of damage to liver parenchymal cells is inherently the synthesis of cholinesterase itself, it is necessary to measure the amount of cholinesterase as protein. In addition, even in the case of a decrease in cholinesterase activity caused by poisoning by organic phosphorous-based agricultural chemicals, measuring the amount of cholinesterase as protein along with enzyme activity allows a more accurate judgment to be made.

Moreover, in the case of the reported enzyme immunoassay methods, since polyclonal antibody is used either for the immobilized antibody or enzyme-labeled antibody, it is difficult to supply a uniform antibody semi-permanently.

Therefore, as a first object of the present invention, the inventors of the present invention attempted to measure the amount of cholinesterase as protein, without being affected by substances (enzymes) other than cholinesterase that have esterase activity and without being affected by cholinesterase activity inhibitors, by using an enzyme immunoassay method that uses monoclonal antibodies that can be supplied semi-permanently in uniform quality without using polyclonal antibodies.

Moreover, since diagnosis of liver cirrhosis and chronic hepatitis by histological examinations using liver tissue specimens obtained by biopsy or operation as performed in the past causes a considerable burden on patients, a method that enables this to be performed by serodiagnosis would be extremely significant. However, the method for determining the ratio of *Aleuria aurantia* lectin-reactive cholinesterase to total enzyme activity of cholinesterase originally present in serum by treating serum with column chromatography using an affinity column on which *Aleuria aurantia* lectin is immobilized and measuring the enzyme activity of *Aleuria aurantia* lectin-reactive cholinesterase retained on the column as reported in the literature involves column chromatography. It is necessary to repeat a complex procedure consisting of adsorption, elution, measurement of volume and measurement of activity, thus making it difficult to measure a large number of samples in a short time.

Therefore, as a second object of the present invention, the inventors of the present invention attempted to develop a method for simultaneously measuring a large number of samples for *Aleuria aurantia* lectin-reactive cholinesterase by a simple procedure and without using column chromatography.

The inventors of the present invention achieved the present invention as a result of earnest studies relating to the above-mentioned problems. Namely, the present invention provides a method for measuring cholinesterase comprising the steps of:

reacting an immobilized first monoclonal antibody that recognizes cholinesterase, a labeled second monoclonal antibody that recognizes an epitope of cholinesterase different from the epitope recognized by said first monoclonal antibody and a sample, and detecting the label of said reacted or unreacted second monoclonal antibody.

Moreover, the present invention provides a method for measuring *Aleuria aurantia* lectin-reactive cholinesterase comprising the step of:

reacting an immobilized monoclonal antibody that recognizes cholinesterase, labeled *Aleuria aurantia* lectin and sample, and a detecting the label of said reacted or unreacted *Aleuria aurantia* lectin.

Moreover, the present invention provides a method for discriminating between liver cirrhosis, liver carcinoma and hepatitis which comprises the step of:

measuring *Aleuria aurantia* lectin-reactive cholinesterase according to the above-mentioned method.

The present invention further provides a kit for measuring cholinesterase comprising a first monoclonal antibody binding to an epitope of cholinesterase and a second monoclonal antibody binding to an epitope of the cholineasterase different from the epitope binding to the first monoclonal antibody.

The present invention also provides a kit for measuring *Aleuria aurantia* lectin-reactive cholinesterase comprising a first monoclonal antibody, and *Aleuria aurantia* lectin.

DETAILED DESCRIPTION OF THE INVENTION

Figure 1:
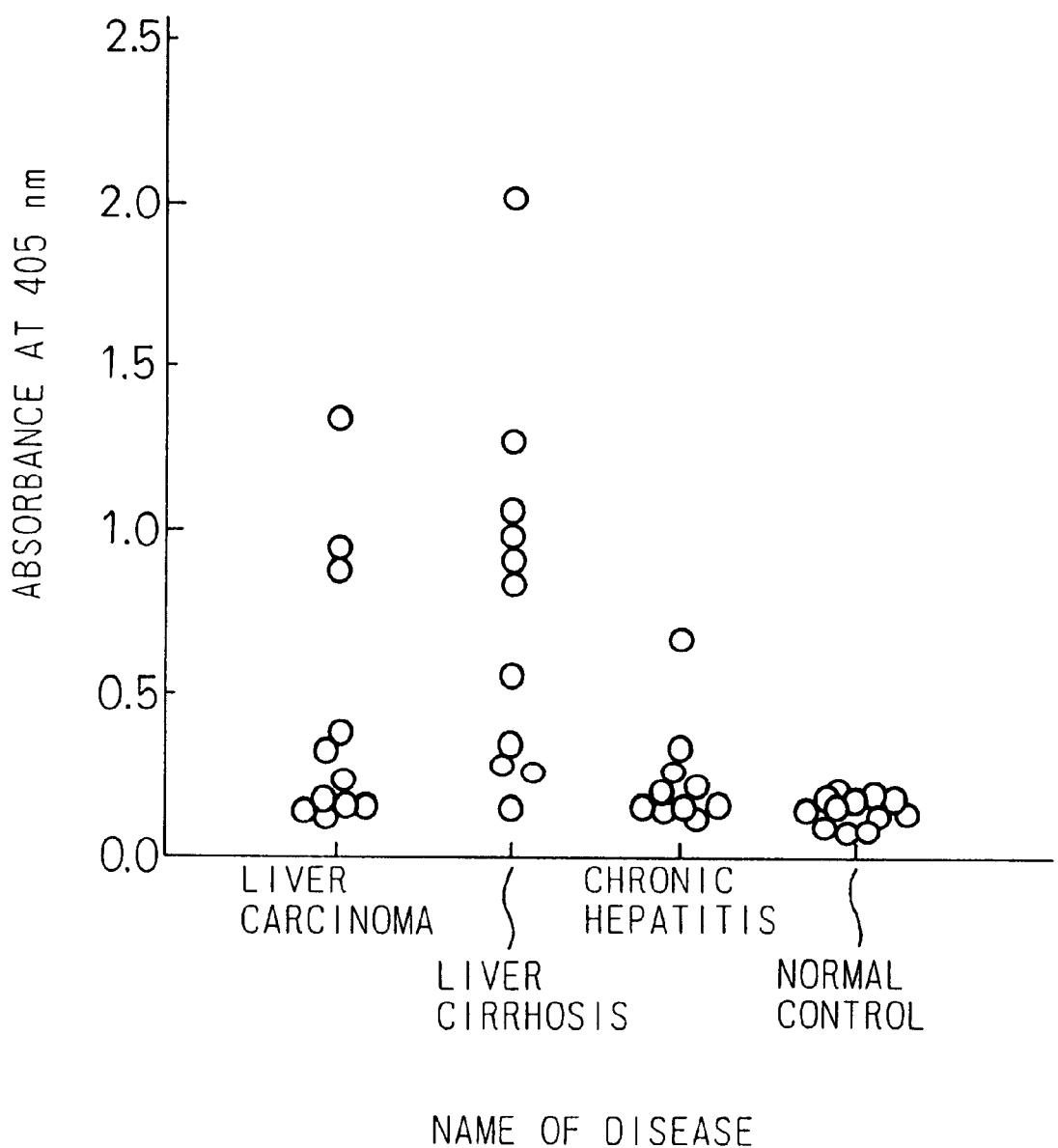
FIG. 1 is a graph showing values for *Aleuria aurantia* lectin-reactive cholinesterase according to disease as measured in step (1) of example 3.

The following provides a detailed explanation of the present invention.

First, an explanation is provided of the first invention. The inventors of the present invention prepared a plurality of monoclonal antibodies specific for cholinesterase, and then examined immunological measurement methods using those monoclonal antibodies.

As a result, the monoclonal antibody relating to the present invention was found to be extremely useful as a reagent for cholinesterase measurement.

The monoclonal antibody in the present invention can be produced by (1) obtaining a hybridoma that produces monoclonal antibody that recognizes cholinesterase by fusing myeloma cells with mouse antibody-producing lymphocytes immunized with cholinesterase prepared from human serum, (2) culturing said hybridoma or a cell line originating from said hybridoma, and (3) collecting said monoclonal antibody from that culture. Hybridomas that produce a monoclonal antibody that recognizes cholinesterase can be produced by cell fusion methods that are known.

In the present invention, a plurality of monoclonal antibodies that recognize different epitopes of said cholinesterase are obtained by using the method described above. Since cholinesterase is a tetramer composed of four identical subunits, although it is possible to measure it using a solid phase enzyme immunoassay method according to the sandwich method using a single monoclonal antibody, there is the possibility of competition occurring between a first antibody and a second antibody. In the present invention, measurement is carried out using a solid phase enzyme immunoassay method according to the sandwich method using two types of monoclonal antibodies recognizing different epitopes.

In the present invention, a monoclonal antibody that recognizes cholinesterase is immobilized for use as the first antibody. Known methods can be used for this immobilization method.

Examples of substances preferably used to immobilize the antibody include beads and microplates made from, for example, glass, polyethylene, polyvinyl chloride, latex, agarose, cellulose and polymethacrylate.

In addition, there are no limitations whatsoever on the labeling methods and means for labeling the second antibody, as well as detection methods and means, and these can be carried out using known methods and means. In methods in which an enzyme such as alkaline phosphatase, peroxidase or β-D-galactosidase is used, a radioactive substance, $^{125}$I, $^{3}$H or so forth, is normally used for the labeling agent, while in methods in which a fluorescent substance is used, fluorescein isocyanate and so forth are normally used for the labeling agent. However, other substances may also be used.

In the case where the labeling agent is an enzyme, a substrate is used to measure its activity. Examples of substrates of alkaline phosphatase include p-nitrophenylphosphate and 4-methylumbelliferylphosphate; examples of substrates of horseradish peroxidase include 2,2'-azinodi-[3-ethylbenzothiazolinesulfonate]-2-ammonium salt (abbreviated as ABTS)-$H_2O_2$, 5-aminosalicylate-$H_2O_2$ and o-phenylenediamine-$H_2O_2$; and examples of substrates of β-D-galactosidase include o-nitrophenol-β-D-galactopyranoside. Known reagents such as diluents, washes, reaction stoppers and so forth are used in addition to these substrates for measurement purposes.

In the present invention, there are no particular limitations on the order of reaction of the first monoclonal antibody, second monoclonal antibody and sample. They may be reacted simultaneously, or reacted sequentially in any arbitrary order.

In the method of the present invention, cholinesterase in a sample is preferably measured, particularly within a range of 6.25 to 600 ng/ml.

Next, the following provides an explanation of the second invention. In this second invention, although a monoclonal antibody that recognizes cholinesterase is immobilized, a monoclonal antibody the same as or similar to the monoclonal antibody of the above-mentioned first invention can be used for this monoclonal antibody. In general, in the case of obtaining a monoclonal antibody from a hybridoma or a culture of animal cells originating from said hybridoma, since the monoclonal antibody has an *Aleuria aurantia* lectin-reactive carbohydrate chain at the Fc region of the antibody, it is necessary to eliminate this region. For example the Fc region may be removed by performing limited hydrolysis using a protease such as pepsin or papain. Alternatively, a carbohydrate chain-free monoclonal antibody can be obtained by culturing hybridoma or animal cells originating from said hybridoma in a medium to which a carbohydrate chain synthesis inhibitor is added. Alternatively, a monoclonal antibody may be treated with carbohydrate chain decomposing enzyme. Immobilization of the monoclonal antibody from which the carbohydrate chain has been removed should be performed in the same manner as immobilization of the first monoclonal antibody of the above-mentioned first invention.

In addition, there are also no limitations whatsoever on the labeling method and means for labeling the *Aleuria aurantia* lectin, or on its detection method and means. Although these can be performed using known methods and means in the same manner as labeling of the second monoclonal antibody of the above-mentioned first invention, when the labeling agent is an enzyme, if the enzyme itself has a carbohydrate chain that binds with *Aleuria aurantia* lectin, it is necessary to eliminate affinity of the enzyme to *Aleuria aurantia* lectin by removing the carbohydrate chain.

There are no particular limitations on the reaction sequence of the monoclonal antibody, *Aleuria aurantia* lectin and the sample in the present invention. They may be reacted simultaneously or reacted in any arbitrary order. However, allowing the monoclonal antibody and sample to react first followed by reaction of *Aleuria aurantia* lectin after removing unreacted sample is preferable since the effects of substances that bond *Aleuria aurantia* lectin other than cholinesterase in the sample can be removed.

In the measurement method according to the present invention, *Aleuria aurantia* lectin-reactive cholinesterase is measured by measuring α1→2, α1→3 and L-fucose residues present in the carbohydrate chain of cholinesterase instead of measuring the amount of *Aleuria aurantia* lectin-reactive cholinesterase as protein.

A sample without dilution or a suitably diluted sample is used in the reaction in the method for detection of *Aleuria aurantia* lectin-reactive cholinesterase according to the present invention. In addition, measuring after diluting the sample so that the total cholinesterase concentration in the sample reaches a specific value is preferable since values are indicated that reflect the amounts of the α1→2, α1→3 and α1→6 L-fucose present in the carbohydrate chain of cholinesterase with respect to total cholinesterase when comparing a plurality of samples.

In the method of the present invention, since it is difficult to measure the absolute amount of *Aleuria aurantia* lectin-reactive cholinesterase, the amount should be expressed as a relative value using as a reference standard samples for which content of *Aleuria aurantia* lectin-reactive cholinesterase is known.

Next, the following provides an explanation of a third invention. The third invention allows discrimination of liver cirrhosis and chronic hepatitis on the basis of results obtained in the second invention of the present application. As was described in the second invention, although the sample can be used for measurement either without dilution or with-suitable dilution, a dilution or 1/20 is preferable in the case the sample is serum. Measurement is then performed according to the method indicated in the second invention.

When compared with the value of *Aleuria aurantia* lectin-reactive cholinesterase in the serum of normal controls, the value in hepatitis patients is roughly equal, while that of liver cirrhosis patients is significantly higher, thus enabling differentiation between hepatitis and liver cirrhosis. In addition, high values have also been observed in patients with liver carcinoma.

In addition, it is possible to discriminate between hepatitis and liver cirrhosis by comparing the measurement of *Aleuria aurantia* lectin-reactive cholinesterase in the serum of a subject obtained by the method in the second invention against the total cholinesterase concentration in the serum of the same subject. In this case, total cholinesterase concentration is measured separately according to the method of the first invention of the present application or a known method, and then determined by calculation. Alternatively, after measuring total cholinesterase concentration in the sample in advance and then diluting the sample so that total cholinesterase concentration in the sample reaches a specific value, preferably 0.1 to 0.5 μg/ml, the measurement according to the second invention of the present application may be performed. In this method, chronic hepatitis and liver cirrhosis can be differentiated from the amount of α1→2, α1→3 and L-fucose residues present in the carbohydrate chain of cholinesterase with respect to total cholinesterase.

The present first invention is a specific measurement method for cholinesterase, and is not affected in any way by the presence of enzyme reaction inhibitors, and so forth, of cholinesterase. In addition, as the monoclonal antibody used in the present invention can be obtained in large quantity and with uniform quality, the reaction has a high degree of uniformity. It can also be produced industrially.

In addition, the detection method of *Aleuria aurantia* lectin-reactive cholinesterase of the present invention is a simple method that resembles a so-called solid phase enzyme immunoassay, and does not require a complex procedure such as that of affinity chromatography. This method is effective in measuring a large number of samples.

Moreover, the hepatitis and liver cirrhosis discrimination method of the present invention is extremely significant since it provides a serodiagnosis while not causing an excessive burden since it is not performed by a histopathological examination of liver tissue specimens obtained by biopsy or operation as performed in the past.

EXAMPLES

The following provides a description of the present invention through its examples. The present invention is not limited to only these examples, however.

Example 1

Preparation of Anti-cholinesterase Mouse Monoclonal Antibody

Monoclonal antibody to cholinesterase was prepared in accordance with the method of G. Kohler and C. Milstein. Namely, an emulsion, containing a mixture of equal volumes of PBS (phosphate-buffered saline) containing 500 µg/ml of cholinesterase derived from human serum and Freund's complete adjuvant, was intraperitoneally administered twice in 200 µl aliquots each into a BALB/c mouse at an interval of 4 weeks. After confirming the increase in antibody titer in the blood by solid phase enzyme immunoassay using a Horse radish peroxidase-labeled rabbit anti-mouse immunoglobulin antibody and a 96-well plate on which cholinesterase was immobilized, 100 µl of PBS in which 200 µg/ml of cholinesterase was dissolved was intraperitoneally injected into said mouse.

Three days later, the spleen of the mouse was excised and cell fusion was performed with 8-azaguanine-resistant, SP2/0-Ag14 myeloma cells using polyethylene glycol. The cells were cultured in 96-well plates and HAT selection was performed. Hybridoma screening was performed by solid phase enzyme immunoassay using 96-well plates, and hybridoma that produced antibody to cholinesterase was cloned by limiting dilution.

A plurality of hybridomas that recognize cholinesterase were obtained in the manner described above. After flask-culturing the resulting hybridomas, they were intraperitoneally transplanted into BALB/c mice to obtain ascites containing monoclonal antibody. The antibody was then purified by ammonium sulfate precipitation and high-performance liquid chromatography using TSKgel Phenyl-5PW (TOSOH CORPORATION) to obtain a purified monoclonal antibody to cholinesterase.

In addition, after performing limited hydrolysis using pepsin, the F(ab')$_2$ fragment of a monoclonal antibody (B-3) to be used for immobilization in the following example was purified by ammonium sulfate precipitation and high-performance liquid chromatography using TSKgel Phenyl-5PW (TOSOH CORPORATION).

Example 2

Measurement of Total Cholinesterase by Enzyme Immunoassay (1) Preparation of Immobilized Antibody 100 µl of the F(ab')$_2$ fragment of the monoclonal antibody that recognizes cholinesterase (B-3) prepared in Example 1 dissolved at 5 µg/ml in PBS well added to each well of an untreated 96-well microtiter plate (Maxisorp, NUNC), and incubated at 37° C. for 3 hours. Next, the solution of each well was removed, each well was washed twice with PBS followed by the addition of 300 µl of PBS containing 1% BSA (bovine serum albumin) to perform blocking for 16 hours at 4° C. (treatment in which BSA is adsorbed at non-specific binding sites with antigen or antibody on the support). The plate was then stored at 4° C.

(2) Preparation of Enzyme-Labeled Antibody 0.1 ml of a 1% ethanol solution of 1-fluoro-2,4-dinitrobenzene was added to 1 ml of horseradish peroxidase (HRPO) solution dissolved in 0.3 M sodium bicarbonate buffer (pH 8.1) (0.5 mg/ml), and allowed to react for 1 hour at room temperature. Next, 1.0 ml of 0.06 M sodium periodate was added and allowed to react for minutes. After removing unreacted sodium periodate by addition of 1.0 ml of 0.16 M ethylene glycol, the solution was dialyzed against 0.01 M sodium bicarbonate buffer (pH 9.5).

Next, 5 mg of monoclonal antibody (A-2) recognizing an epitope of the antigen different from that recognized by B-3 was added and allowed to react for hours. 5 mg of sodium borohydride was added after which the solution was allowed to stand for 16 hours at 4° C.

The reaction product obtained in this manner was then purified by high-performance liquid chromatography using TSKgel G3000SW (TOSOH CORPORATION) to obtain HRPO-labeled monoclonal antibody.

(3) Measurement of Total Cholinesterase by Enzyme Immunoassay

After returning the microtiter plate, on which antibody was immobilized in step (1) of the present Example, to room temperature and washing twice with PBS, 100 µl aliquots of PBS containing 1% BSA containing 6.25 to 600 ng/ml of purified cholinesterase was added to each well as standard (the concentration of a solution of purified cholinesterase that exhibits an absorbance of 1 at 280 nm was taken to be 1 mg/ml). After incubating for 2 hours at 25° C. and removing the solution, the plate was washed 5 times with PBS containing 0.05% TWEEN-20 (PBS-T) (TWEEN is a trademark of Astra Chem. Ind. Inc. for polyoxyethylene sorbitan mondlaurate). Next, 100 µl aliquots of PBS-T solution containing 0.1% BSA, in which the HRPO-labeled antibody prepared in step (2) was dissolved to a concentration of 4.5 µg/ml, was added to each well. After incubating for 1 hour at 37° C., the solution was removed and the plate was washed 3 times with PBS-T. Moreover, 100 µl aliquots of substrate solution consisting of 0.1 M citrate buffer (pH 4.1) containing 0.6 mg/ml ABTS and 0.01% H$_2$O$_2$ were added to each well. After allowing to react for 15 minutes at room temperature, 100 µl aliquots of 0.2 M oxalic acid were added to each well to stop the reaction.

After stopping the reaction, absorbance was measured for each well by an automated microtiter plate reader at a measuring wavelength of 415 nm and reference wavelength of 600 nm. The result shown in Table 1 was obtained from the concentration and absorbance of the standard.

TABLE 1

| Cholinesterase Concentration (ng/ml) | Absorbance at 415 nm |
|---|---|
| 0 | 0.077 |
| 6.25 | 0.089 |
| 12.5 | 0.100 |
| 25.0 | 0.131 |
| 50.0 | 0.175 |
| 100.0 | 0.273 |
| 200.0 | 0.480 |
| 400.0 | 1.020 |
| 600.0 | 1.592 |

In addition, the same procedure was performed using a 1:100 dilution of human serum diluted with PBS containing 1% BSA for the sample instead of the standard. The total amount of cholinesterase in the serum was determined by converting the concentration using the calibration curve obtained from the standard. Those result was shown in Table 2.

TABLE 2

| Sample Number | Cholinesterase Concentration (μg/ml) |
| --- | --- |
| 1 | 21.4 |
| 2 | 28.0 |
| 3 | 19.0 |
| 4 | 16.7 |
| 5 | 8.9 |
| 6 | 13.1 |
| 7 | 13.7 |
| 8 | 18.5 |
| 9 | 18.7 |
| 10 | 22.9 |

Example 3

Detection of *Aleuria aurantia* Lectin-reactive Cholinesterase in Serum

1) Detection of *Aleuria Aurantia* Lectin-Reactive Cholinesterase in a Sample Having an Equal Concentration of Cholinesterase The total cholinesterase concentration in serum was measured in advance using the method of step (3) of Example 2. Samples were prepared by diluting with PBS containing 10% BSA so that each serum sample had a cholinesterase concentration of 0.5 μg/ml. After returning a microtiter plate prepared in the same manner as step (1) of example 2 to room temperature and washing twice with PBS, 100 μl of sample having an equal concentration of cholinesterase well added and incubated for 2 hours at 25° C. After removing the solution, the microtiter plate was washed 5 times with PBS containing 0.05% TWEEN-20 (PBS-T) and 3 times with PBS.

Next, 100 μl aliquots of PBS containing 4 μg/ml of biotin-labeled *Aleuria aurantia* lectin (Honen Co., Ltd.) and 4 μg/ml of streptoavidin-labeled alkaline phosphatase (Jackson Immunoresearch Laboratories Inc.) were added to each well followed by incubation for 2 hours at 25° C. After removing the solution and washing 4 times with PBS, 100 μl aliquots of 10 mM p-nitrophenylphosphate, 2 mM $MgCl_2$ and 0.3 M 2-amino-2-methyl-1-propanol were added to each well followed by incubation for 10 minutes at 25° C. After stopping the reaction by addition of 100 μl of 1 N NaOH, absorbance at a wavelength of 405 nm and reference wavelength of 492 nm were measured for each well by an automated microtiter plate reader. The result shown in FIG. 1 was obtained after classification into hepatocellular carcinoma patients, liver cirrhosis patients, chronic hepatitis patients and normal controls.

Figure 2:
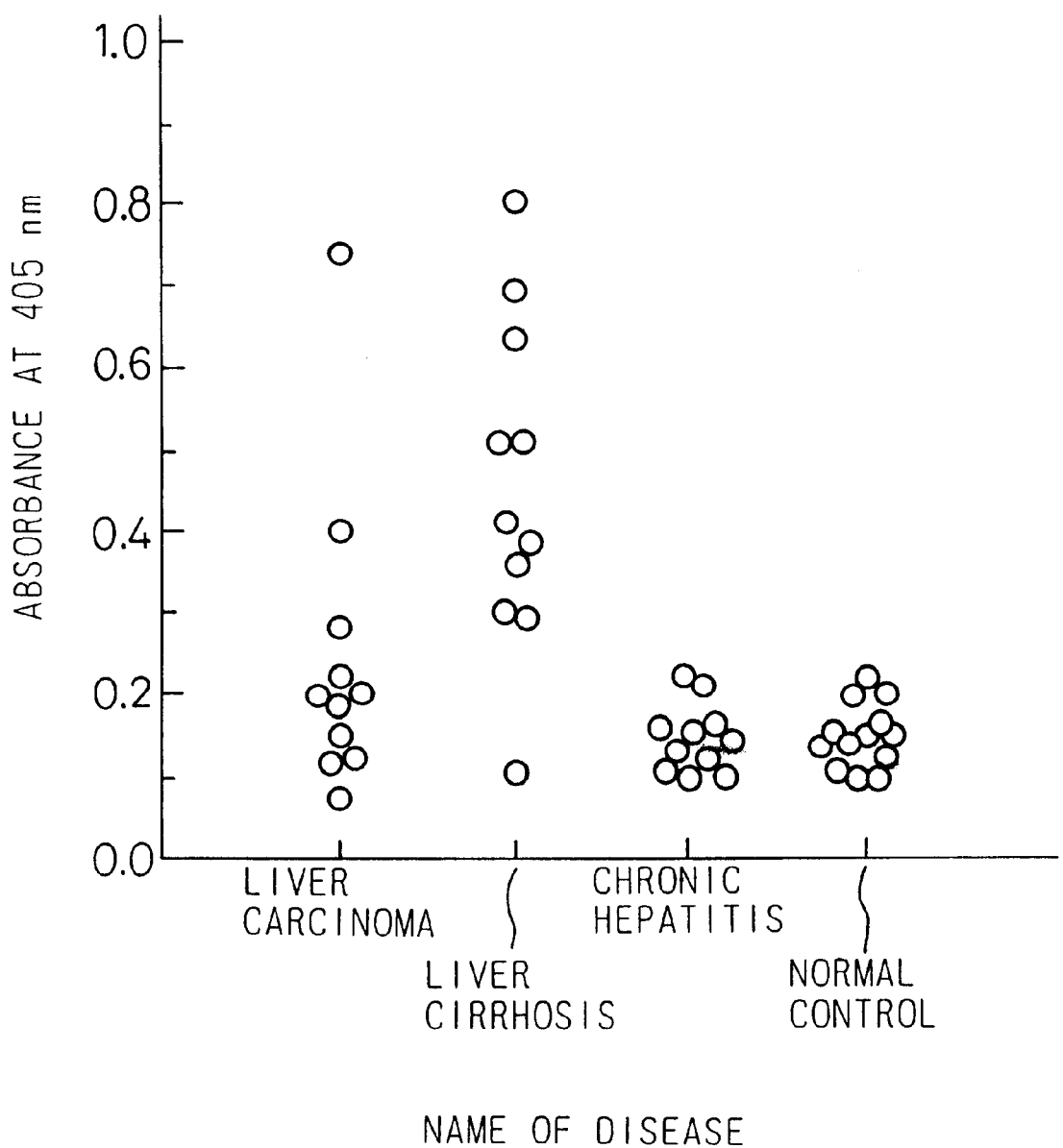
FIG. 2 is a graph showing values for *Aleuria aurantia* lectin-reactive cholinesterase according to disease as measured in step (2) of example 3.

(2) Detection of *Aleuria Aurantia* lectin-Reactive Cholinesterase Using Serum Samples Diluted by the Same Dilution Factor With the exception of using serum diluted 1:10 with PBS containing 10% BSA for the samples, and using the F(ab')2 fragment of monoclonal antibody (B-3) immobilized in each well of the microtiter plate at a concentration of 3 μg/ml, detection of *Aleuria aurantia* lectin-reactive cholinesterase was performed using the same method as step (1) of Example 3. The result shown in FIG. 2 was obtained after classifying into hepatocellular carcinoma patients, cirrhosis patients, chronic hepatitis patients and normal controls.

For both the result of detection of *Aleuria aurantia* lectin-reactive cholinesterase when serum having equal concentration of cholinesterase was used for the samples (FIG. 1), and the result of detection of *Aleuria aurantia* lectin-reactive cholinesterase when serum diluted by the same dilution factor was used for the samples (FIG. 2), values were low in chronic hepatitis patients and normal controls and high in liver cirrhosis patients. Thus, either method can be used to discriminate between chronic hepatitis (hepatitis) and liver cirrhosis by serodiagnosis.

What is claimed is:

1. A method of measuring *Aleuria aurantia* lectin (AAL)-reactive carbohydrate chains of cholinesterase in a serum sample comprising the steps of:
    (a) reacting the serum sample with
        (i) an immobilized F(ab')$_2$ monoclonal antibody which specifically binds to cholinesterase;
        (ii) adding a labeled *Aleuria aurantia* lectin (AAL); and
    (b) measuring an amount of fucose of labeled AAL-reactive carbohydrate chains of cholinesterase in said serum sample.

2. A kit for measuring *Aleuria aurantia* lectin-reactive carbohydrate chains of cholinesterase comprising:
    (a) an immobilized F(ab')$_2$ monoclonal antibody which specifically binds to cholinesterase; and
    (b) *Aleuria aurantia* lectin.

3. A method for discriminating between liver cirrhosis or liver carcinoma and chronic hepatitis comprising the steps of:
    (a) reacting a serum sample from a subject suspected of having liver cirrhosis, liver carcinoma, or chronic hepatitis with;
        (i) an immobilized F(ab')$_2$ monoclonal antibody which specifically binds to cholinesterase, and
        (ii) a labeled *Aleuria aurantia* lectin (AAL);
    (b) measuring an amount of fucose of labeled AAL reactive carbohydrate chains of cholinesterase in the sample from said subject to obtain a value of AAL lectin reactive cholinesterase; and
    (c) comparing the value of AAL reactive cholinesterase in the sample from said subject with a value of AAL reactive cholinesterase in a sample from a healthy control subject thereby determining whether the value of AAL reactive cholinesterase in the serum sample of said subject is higher than or about the same as the value of said control subject.

4. A method for discriminating between liver cirrhosis or liver carcinoma and chronic hepatitis comprising the steps of:
    (a) reacting a serum sample from a subject having liver cirrhosis, liver carcinoma, or hepatitis with;
        (i) an immobilized F(ab')$_2$ monoclonal antibody which specifically binds to cholinesterase, and
        (ii) a labeled *Aleuria aurantia* lectin (AAL);
    (b) measuring an amount of fucose of labeled AAL reactive carbohydrate chains of cholinesterase in the sample from said subject to obtain a value of AAL reactive cholinesterase; and
    (c) comparing the value of AAL reactive cholinesterase in the sample from said subject with a value of total cholinesterase in the sample from said subject thereby determining whether the compared result for the serum sample of said subject is higher than or about the same as normal controls.

5. A method for discriminating between liver cirrhosis or liver carcinoma and chronic hepatitis comprising the steps of:

(a) measuring total cholinesterase in a serum sample from a subject having liver cirrhosis, liver carcinoma, or hepatitis, and then diluting the sample; and (b) reacting the diluted serum sample from said subject with;
  (i) an immobilized F(ab')$_2$ monoclonal antibody which specifically binds to cholinesterase, and
  (ii) a labeled *Aleuria aurantia* lectin (AAL); and (c) measuring an amount of fucose of labeled AAL reactive carbohydrate chains of cholinesterase in the diluted sample from said subject to obtain a value of AAL reactive cholinesterase; and (d) comparing the value of AAL reactive cholinesterase in the sample from said subject with a value of total cholinesterase in the sample from said subject thereby determining whether the compared result for the serum sample of said subject is higher than or about the same as normal controls.

* * * * *